US011141136B2

(12) United States Patent
Funakubo

(10) Patent No.: US 11,141,136 B2
(45) Date of Patent: Oct. 12, 2021

(54) ULTRASOUND OBSERVATION DEVICE, PROCESSING DEVICE, METHOD OF OPERATING ULTRASOUND OBSERVATION DEVICE, AND COMPUTER READABLE RECORDING MEDIUM

(71) Applicant: OLYMPUS CORPORATION, Tokyo (JP)

(72) Inventor: Sho Funakubo, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 549 days.

(21) Appl. No.: 16/008,104

(22) Filed: Jun. 14, 2018

(65) Prior Publication Data
US 2018/0289360 A1 Oct. 11, 2018

Related U.S. Application Data

(63) Continuation of application No. PCT/JP2016/081348, filed on Oct. 21, 2016.

(30) Foreign Application Priority Data

Dec. 17, 2015 (JP) .............................. JP2015-246697

(51) Int. Cl.
*A61B 8/00* (2006.01)
*A61B 8/08* (2006.01)
(Continued)

(52) U.S. Cl.
CPC ............ *A61B 8/5207* (2013.01); *A61B 8/463* (2013.01); *A61B 8/467* (2013.01);
(Continued)

(58) Field of Classification Search
CPC ....... A61B 8/5207; A61B 8/467; A61B 8/463; A61B 8/14; A61B 8/12; A61B 8/54;
(Continued)

(56) References Cited

U.S. PATENT DOCUMENTS

2009/0267921 A1* 10/2009 Pryor .................. G06F 3/04883
345/177
2012/0029353 A1* 2/2012 Slayton .................... A61N 7/00
600/439
(Continued)

FOREIGN PATENT DOCUMENTS

JP 2012-019824 A 2/2012
JP 2015-198810 A 11/2015

OTHER PUBLICATIONS

International Search Report dated Dec. 27, 2016 issued in PCT/JP2016/081348.

*Primary Examiner* — Joel Lamprecht
(74) *Attorney, Agent, or Firm* — Scully, Scott, Murphy & Presser, P.C.

(57) ABSTRACT

A processing device includes a controller including hardware. The controller is configured to execute: generating an ultrasound image based on an ultrasound signal acquired by an ultrasound probe, the ultrasound probe being configured to transmit an ultrasonic wave to a subject that is an observation target and receive an ultrasonic wave reflected by the subject; generating shift information including a shift direction of a display area of the ultrasound image displayed on a display unit in accordance with a command position with respect to the ultrasound image; shifting the ultrasound image in accordance with the shift information; and generating a character image indicating an area targeted for a process performed on the ultrasound image in relation to the command position in the ultrasound image after being shifted.

15 Claims, 13 Drawing Sheets

(51) Int. Cl.
*G01S 7/52* (2006.01)
*G01S 15/89* (2006.01)
*G06F 3/0481* (2013.01)
*G06F 3/01* (2006.01)
*G06F 3/0484* (2013.01)
*G06F 3/0488* (2013.01)
*A61B 8/14* (2006.01)
*A61B 8/12* (2006.01)

(52) U.S. Cl.
CPC ...... *G01S 7/52073* (2013.01); *G01S 7/52084* (2013.01); *G01S 7/52085* (2013.01); *G01S 15/8906* (2013.01); *G01S 15/8922* (2013.01); *G06F 3/013* (2013.01); *G06F 3/017* (2013.01); *G06F 3/0488* (2013.01); *G06F 3/04815* (2013.01); *G06F 3/04845* (2013.01); *A61B 8/12* (2013.01); *A61B 8/14* (2013.01); *A61B 8/54* (2013.01)

(58) Field of Classification Search
CPC ............. G01S 7/52073; G01S 15/8922; G01S 7/52084; G01S 7/52085; G01S 15/8906; G06F 3/04815; G06F 3/017; G06F 3/013; G06F 3/04845; G06F 3/0488
See application file for complete search history.

(56) References Cited

U.S. PATENT DOCUMENTS

| | | |
|---|---|---|
| 2015/0289844 A1 | 10/2015 | Okamoto |
| 2016/0007965 A1* | 1/2016 | Murphy .............. G06F 3/04845 345/173 |
| 2016/0228091 A1* | 8/2016 | Chiang ................ A61B 8/0883 |

* cited by examiner

ULTRASOUND OBSERVATION DEVICE, PROCESSING DEVICE, METHOD OF OPERATING ULTRASOUND OBSERVATION DEVICE, AND COMPUTER READABLE RECORDING MEDIUM

CROSS-REFERENCE TO RELATED APPLICATION

This application is a continuation of PCT international application Ser. No. PCT/JP2016/081348 filed on Oct. 21, 2016 which designates the United States, incorporated herein by reference, and which claims the benefit of priority from Japanese Patent Applications No. 2015-246697, filed on Dec. 17, 2015, incorporated herein by reference.

BACKGROUND

The present disclosure relates to an ultrasound observation device that observes an observation target by using ultrasonic waves, a processing device, a method of operating the ultrasound observation device, and a computer readable recording medium.

Ultrasonic waves are sometimes used to observe the characteristics of a living tissue or material that is an observation target. Specifically, ultrasonic waves are transmitted to the observation target and predetermined signal processing is performed on ultrasound echoes reflected by the observation target so that the information related to the characteristics of the observation target is acquired.

Ultrasound diagnostic devices with an ultrasound transducer provided in the distal end of an insertion unit are used for diagnosis of living tissues, or the like, inside a body to which ultrasonic waves are applied. In ultrasound diagnostic devices, an ultrasound transducer acquires ultrasound echoes, and a monitor displays acquired ultrasound images in chronological order.

An operator such as a doctor inserts an insertion unit into the inside of a body and then operates an operating unit at hand while conducting diagnosis on the basis of information (ultrasound image) based on ultrasound echoes. Here, the operator diagnoses ultrasound images by making command input for a process to set an observation area, a measurement process, or the like. For example, on an ultrasound image, command inputs are made for two measurement points for measuring a distance, and the distance between the measurement points is measured. As a diagnosis system for conducting diagnosis as described above, a technology for directly making command input to ultrasound images by using a touch panel is disclosed (for example, see Japanese Laid-open Patent Publication No. 2012-19824). According to Japanese Laid-open Patent Publication No. 2012-19824, a process is performed to display an image including a touch button indicating the position that corresponds to a touch position of a finger of the operator and a caliper that is adjacent to the touch button and that indicates a command position on the image. Thus, it is possible to perform operation such as adjustment on a command position while the visibility of a command position (caliper) is retained without hiding the command position with the finger of the operator.

SUMMARY

A processing device according to one aspect of the present disclosure includes a controller including hardware, wherein the controller is configured to execute: generating an ultrasound image based on an ultrasound signal acquired by an ultrasound probe, the ultrasound probe being configured to transmit an ultrasonic wave to a subject that is an observation target and receive an ultrasonic wave reflected by the subject; generating shift information including a shift direction of a display area of the ultrasound image displayed on a display unit in accordance with a command position with respect to the ultrasound image; shifting the ultrasound image in accordance with the shift information; and generating a character image indicating an area targeted for a process performed on the ultrasound image in relation to the command position in the ultrasound image after being shifted.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
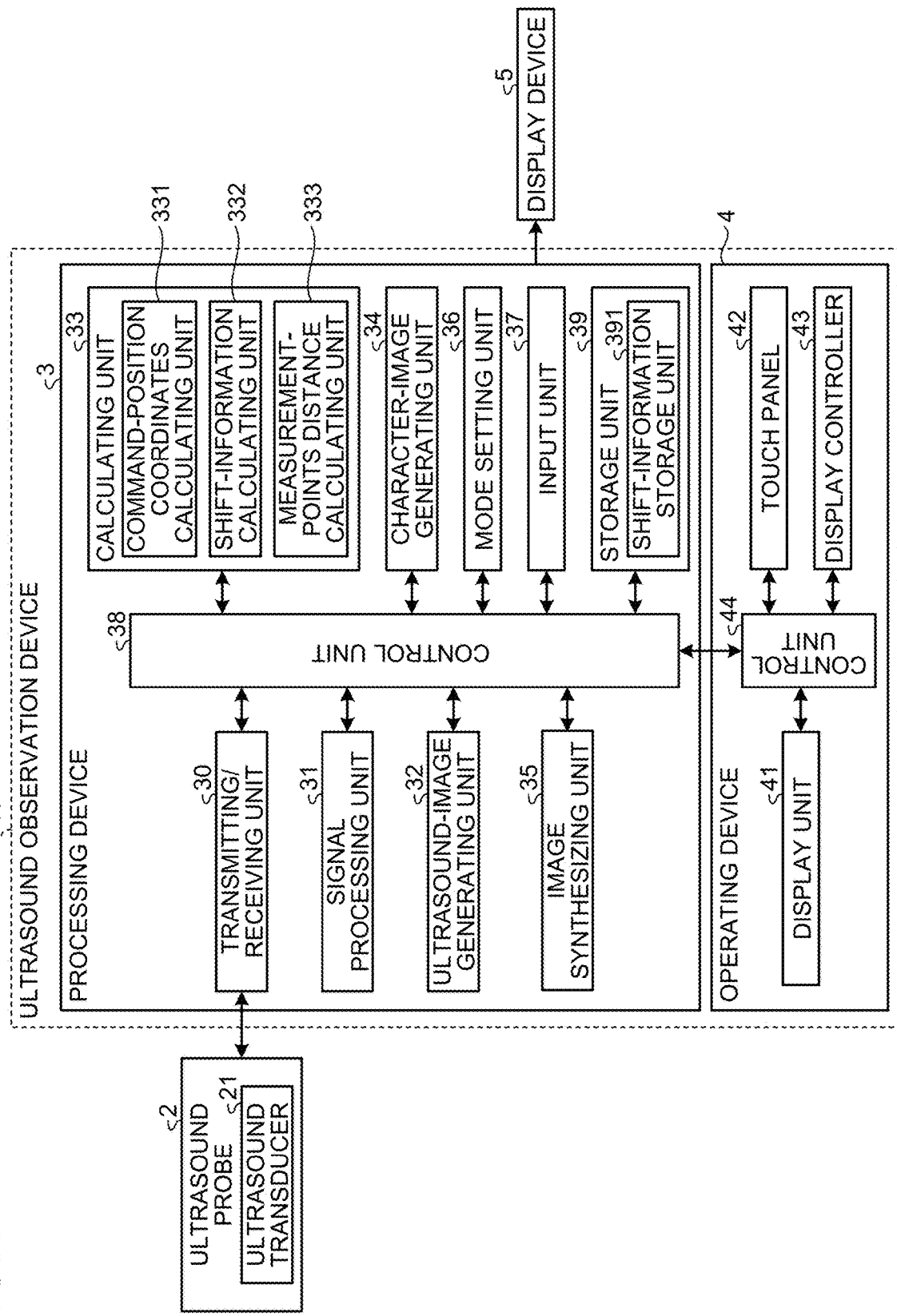
FIG. 1 is a block diagram that illustrates a configuration of an ultrasound diagnosis system according to a first embodiment.

With reference to attached drawings, an explanation is given below of an aspect (hereinafter, referred to as "embodiment") for implementing the present disclosure. In the following explanation, an ultrasound diagnosis system and an ultrasound endoscope system including a medical diagnostic apparatus that generates ultrasound images based on ultrasound echoes are described; however, the embodiment is not a limitation on the present disclosure. Furthermore, the same components are attached with the same reference numeral in explanation.

First Embodiment

FIG. 1 is a block diagram that illustrates a configuration of an ultrasound diagnosis system according to a first embodiment. An ultrasound diagnosis system 1 illustrated in FIG. 1 is a device that observes an observation target by using ultrasonic waves and that includes a processing device according to the present disclosure.

The ultrasound diagnosis system 1 includes an ultrasound probe 2 that receives ultrasound echoes reflected after ultrasonic waves are output; a processing device 3 that generates images based on ultrasound echoes acquired by the ultrasound probe 2; an operating device 4 that is capable of simultaneously receiving multiple pieces of input command information and outputs the received information to the processing device 3 to operate the processing device 3; and a display device 5 that displays various types of information including images generated based on ultrasound echoes by the processing device 3. The display device 5 is implemented by using a display panel such as a liquid crystal or organic electro luminescence (EL). According to the present embodiment, the processing device 3 and an operating device 4 constitute an ultrasound observation device 10.

An ultrasound transducer 21 that outputs ultrasound pulses to the observation target and receives ultrasound echoes reflected by the observation target is provided at the distal end of the ultrasound probe 2.

Here, if the observation target is a living tissue, the ultrasound transducer 21 may have any of the configurations as an extracorporeal probe that emits ultrasonic waves from the body surface of a living body, as a miniature ultrasound probe including an insertion unit with a long axis that is inserted into a lumen such as digestive tract, biliopancreatic duct, or blood vessel, and as an ultrasound endoscope further including an optical system in an intraluminal ultrasound probe. Among them, when the configuration of an ultrasound endoscope is used, the ultrasound transducer 21 is provided at the distal end side of the insertion unit of the intraluminal ultrasound probe, and the intraluminal ultrasound probe is removably connected to the processing device 3 at the proximal end side.

The ultrasound transducer 21 converts electrical pulse signals received from the processing device 3 into ultrasound pulses (sound pulse signals) and converts ultrasound echoes reflected by an external specimen into electrical echo signals. With regard to the ultrasound transducer 21, the ultrasound transducer may conduct scanning mechanically or a plurality of ultrasound transducers may conduct scanning electronically. According to the first embodiment, an explanation is given of a case where a radial-type ultrasound transducer is used.

The processing device 3 includes a transmitting/receiving unit 30, a signal processing unit 31, an ultrasound-image generating unit 32, a calculating unit 33, a character-image generating unit 34, an image synthesizing unit 35, a mode setting unit 36, an input unit 37, a control unit 38, and a storage unit 39.

The transmitting/receiving unit 30 transmits and receives electric signals to and from the ultrasound transducer 21. The transmitting/receiving unit 30 is electrically connected to the ultrasound transducer 21 so that it transmits electric pulse signals to the ultrasound transducer 21 and receives echo signals that are electric reception signals from the ultrasound transducer 21. Specifically, the transmitting/receiving unit 30 generates electric pulse signals on the basis of a predetermined waveform and transmission timing and transmits the generated pulse signals to the ultrasound transducer 21.

The transmitting/receiving unit 30 amplifies echo signals. The transmitting/receiving unit 30 conducts sensitivity time control (STC) correction to amplify echo signals having a larger receiving depth with a higher amplification factor. After conducting processing such as filtering on amplified echo signals, the transmitting/receiving unit 30 conducts A/D conversion to generate digital high-frequency (RF: radio frequency) data in time domain and outputs it.

The signal processing unit 31 generates digital B-mode reception data based on RF data received from the transmitting/receiving unit 30. Specifically, the signal processing unit 31 performs known processing such as bandpass filtering, envelope detection, or logarithmic conversion on RF data to generate digital B-mode reception data. For logarithmic conversion, RF data is divided by the reference voltage, and the common logarithm of a resultant is represented by a decibel value. The signal processing unit 31 outputs the generated B-mode reception data to the ultrasound-image generating unit 32. The signal processing unit 31 is implemented by using various types of arithmetic circuits such as a central processing unit (CPU).

The ultrasound-image generating unit 32 generates ultrasound image data based on B-mode reception data received from the signal processing unit 31. The ultrasound-image generating unit 32 performs image processing using a known technology such as gain processing or contrast processing on B-mode reception data and decimates data that corresponds to a data step width defined based on the display range of an image on the display device 5, or the like, thereby generating B-mode image data. B-mode images are gray-scaled images in which the values of R (red), G (green), and B (blue), which are variables when the RGB color system is used as a color space, are identical.

The ultrasound-image generating unit 32 performs coordinates conversion on B-mode reception data from the signal processing unit 31 to rearrange a scan area so as to be properly represented in space and then performs an interpolation process on the B-mode reception data to fill gaps in the B-mode reception data, thereby generating B-mode image data. The ultrasound-image generating unit 32 outputs the generated B-mode image data to the image synthesizing unit 35.

After receiving a command input from the operating device 4, the calculating unit 33 performs a calculation process in accordance with the command input. Specifically, the calculating unit 33 conducts position calculation for the display position of a character image (e.g., a measurement point) in an ultrasound image in accordance with an operation that is input when a command position in the ultrasound image is changed. The calculating unit 33 includes a command-position coordinates calculating unit 331, a shift-information calculating unit 332, and a measurement-points distance calculating unit 333.

The command-position coordinates calculating unit 331 calculates the coordinates of a command position on the B-mode image that is displayed on a display unit 41, described later, from the contact position on a touch panel 42, described later, based on operating signals.

The shift-information calculating unit 332 calculates the amount of shift of a B-mode image on the basis of a command position (coordinates calculated by the command-position coordinates calculating unit 331), a distance that is a distance from the ultrasound transducer 21 and that is a distance (depth) from the center of an image of the ultrasound transducer to the position that corresponds to a command position in the B-mode image, the type of the ultrasound transducer, and the like, and outputs the calculated amount of shift and the preset shift direction as shift information.

The measurement-points distance calculating unit 333 calculates the distance between two measurement points in an ultrasound image, confirmed on the basis of a command position (coordinates calculated by the command-position coordinates calculating unit 331). Furthermore, the measurement-points distance calculating unit 333 calculates the actual distance on the basis of the calculated distance between measurement points.

Upon receiving command inputs from the operating device 4, the character-image generating unit 34 generates character image data including a character image in which characters that correspond to the command inputs, e.g., two measurement points for measuring a distance, are located based on command input positions (coordinates) calculated by the calculating unit 33. Character image data may include information to be related to a B-mode image, such as a frame number, in addition to the above-described character image. The character-image generating unit 34 outputs the generated character image data to the image synthesizing unit 35.

The image synthesizing unit 35 generates synthesis image data including a synthesis image that is a synthesis of a B-mode image and a character image by using image data (B-mode image data and character image data) generated by each of the ultrasound-image generating unit 32 and the character-image generating unit 34. Synthesis image data includes information such as a frame number in addition to the above-described synthesis image.

Upon receiving a command input from the operating device 4, the mode setting unit 36 sets an operation mode that corresponds to the command input. Specifically, in accordance with a command input, the mode setting unit 36 sets any operation mode, such as a distance measurement mode, a command input mode, or an enlargement/reduction mode, as a processing mode for performing processing on a B-mode image.

The input unit 37 is implemented by using an input button for receiving input of various types of information to turn on/off the power source, or the like.

The control unit 38 performs overall control on the ultrasound diagnosis system 1. The control unit 38 is implemented by using a central processing unit (CPU), various arithmetic circuits, or the like, having calculation and control functions. The control unit 38 reads, from the storage unit 39, information stored and saved in the storage unit 39, and performs various calculation operations related to a method of operating the ultrasound observation device 10, thereby performing overall control on the ultrasound observation device 10. Furthermore, the control unit 38 may be configured by using a CPU, or the like, that is shared by the signal processing unit 31.

The storage unit 39 stores various programs for operating the ultrasound diagnosis system 1, data including various parameters needed for operation of the ultrasound diagnosis system 1, and the like. Furthermore, the storage unit 39 includes a shift-information storage unit 391 that stores the amount of shift calculated by the shift-information calculating unit 332 in relation to a command position (coordinates calculated by the command-position coordinates calculating unit 331), a distance (depth) from the ultrasound transducer, the type of ultrasound transducer, and the like.

Furthermore, the storage unit 39 stores various programs including an operation program to implement a method of operating the ultrasound diagnosis system 1. The operation program may be widely distributed by being recorded in a recording medium readable by a computer, such as hard disk, flash memory, CD-ROM, DVD-ROM, or flexible disk. Furthermore, the above-described various programs may be acquired by being downloaded via a communication network. The communication network mentioned here is implemented by using, for example, an existing public network, local area network (LAN), or wide area network (WAN), and it may be wired or wireless.

The storage unit 39 having the above-described configuration is implemented by using a read only memory (ROM) that has various programs, and the like, previously installed, a random access memory (RAM) that stores calculation parameters, data, and the like, for each process.

The operating device 4 includes the display unit 41, the touch panel 42 (multi-input receiving unit), a display controller 43, and a control unit 44.

The display unit 41 is configured by using a display panel that is made of liquid crystal, organic electro luminescence (EL), or the like. The display unit 41 displays ultrasound images that correspond to B-mode image data and various types of information related to operation, which are input via for example the control units 38, 44.

The touch panel 42 is provided on the display screen of the display unit 41, and it receives an input that corresponds to the contact position of an object from outside. Specifically, the touch panel 42 detects a touch (contact) position of a user such as operator in accordance with an operation icon displayed on the display unit 41, and it outputs the operating signal including the position (coordinates) that corresponds to the detected touch position to the control unit 44. As the display unit 41 displays ultrasound images and various types of information, the touch panel 42 functions as a graphical user interface (GUI). The touch panel has a resistive layer system, a capacitive system, an optical system, or the like, and a touch panel with any system is applicable.

The display controller 43 controls the display unit 41 so as to display synthesis image data generated by the image synthesizing unit 35 after it is acquired and controls the display unit 41 so as to display a guide image for input operation through the touch panel 42 and a display image that corresponds to an operation mode.

The control unit 44 performs overall control of the operating device 4. The control unit 44 is implemented by using a central processing unit (CPU), various arithmetic circuits, or the like, having calculation and control functions.

Figure 2:
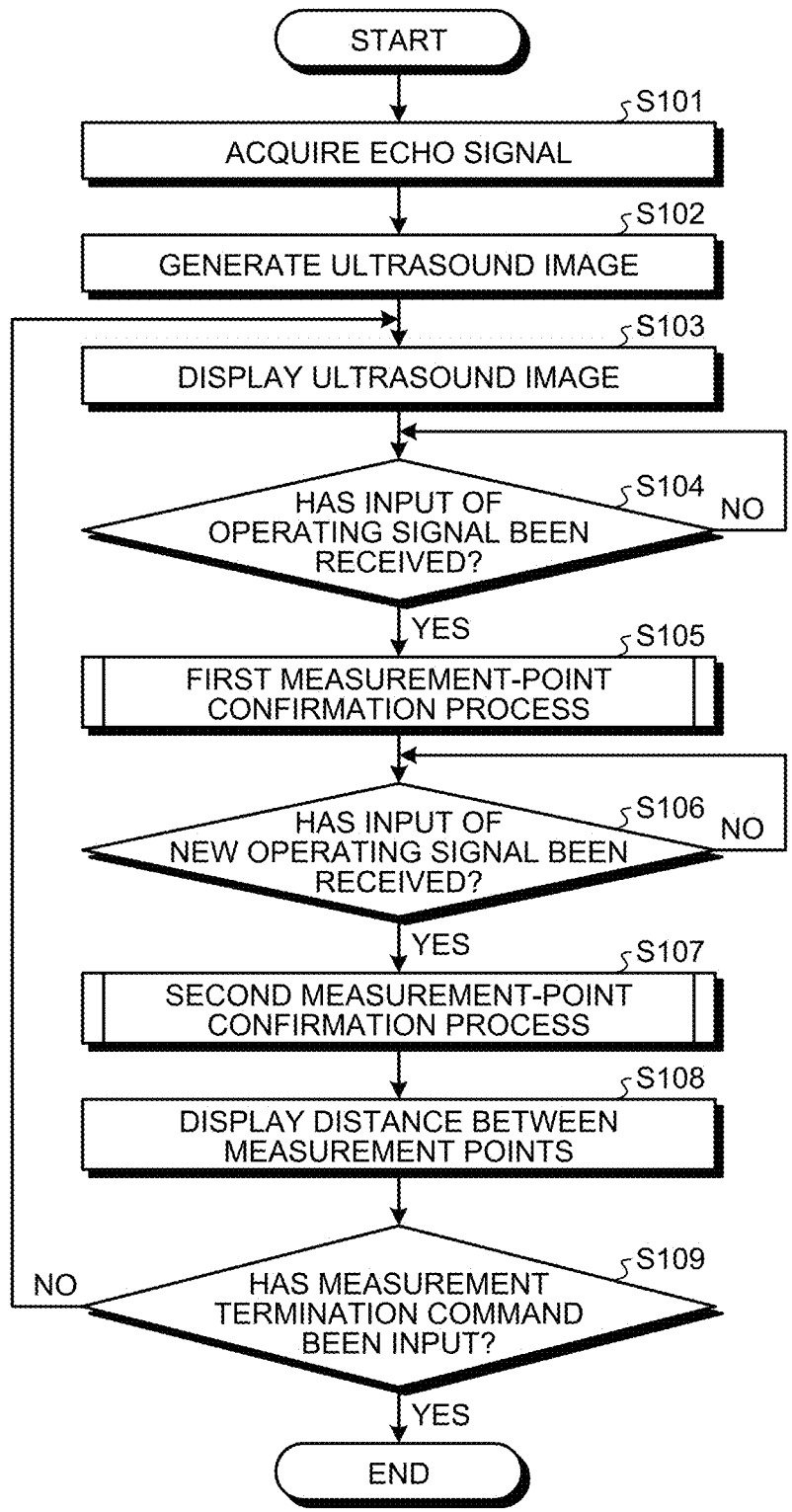
FIG. 2 is a flowchart that illustrates a measurement process performed by the ultrasound diagnosis system according to the first embodiment.

Next, with reference to the drawings, an explanation is given of a measurement process performed by the ultrasound observation device 10 in the ultrasound diagnosis system 1 having the above-described configuration. FIG. 2 is a flowchart that illustrates a measurement process performed by the ultrasound diagnosis system according to the first embodiment. Furthermore, an explanation is given below of a case where each unit operates in a distance measurement mode for measuring the distance between designated measurement points under the control of the control unit 38.

After the transmitting/receiving unit 30 acquires an echo signal from the ultrasound transducer 21 (Step S101), the control unit 38 performs control to generate an ultrasound image (here, B-mode image) based on the echo signal. The signal processing unit 31 and the ultrasound-image generating unit 32 generate B-mode image data including the B-mode image based on the acquired echo signal (Step S102: ultrasound-image generation step). Then, the control unit 38 outputs a control signal together with the B-mode image data to the operating device 4 so that at least the display unit 41 displays the generated B-mode image. Thus, under the control of the display controller 43, the display unit 41 displays a B-mode image (Step S103). In the following explanation, the display unit 41 displays freeze images; however, live images may be displayed.

Then, the control unit 38 determines whether an input (touch input) of an operating signal has been received from the control unit 44 (the touch panel 42) (Step S104). If an input of an operating signal has been received (Step S104: Yes), the control unit 38 proceeds to Step S105. Conversely, if an input of an operating signal has not been received (Step S104: No), the control unit 38 repeatedly checks whether an operating signal has been input.

After receiving an operating signal from the operating device 4, the control unit 38 performs a process to confirm one of the two measurement points (command positions) for measurement on the basis of the operating signal (Step S105: a first measurement-point confirmation process). Specifically, the calculating unit 33 performs a process to calculate a command position in accordance with a command input from the touch panel 42, while the operating device 4 causes the display unit 41 to display a measurement point (command position) superimposed on the B-mode image, whereby the process to confirm the measurement point is performed.

Figure 3:
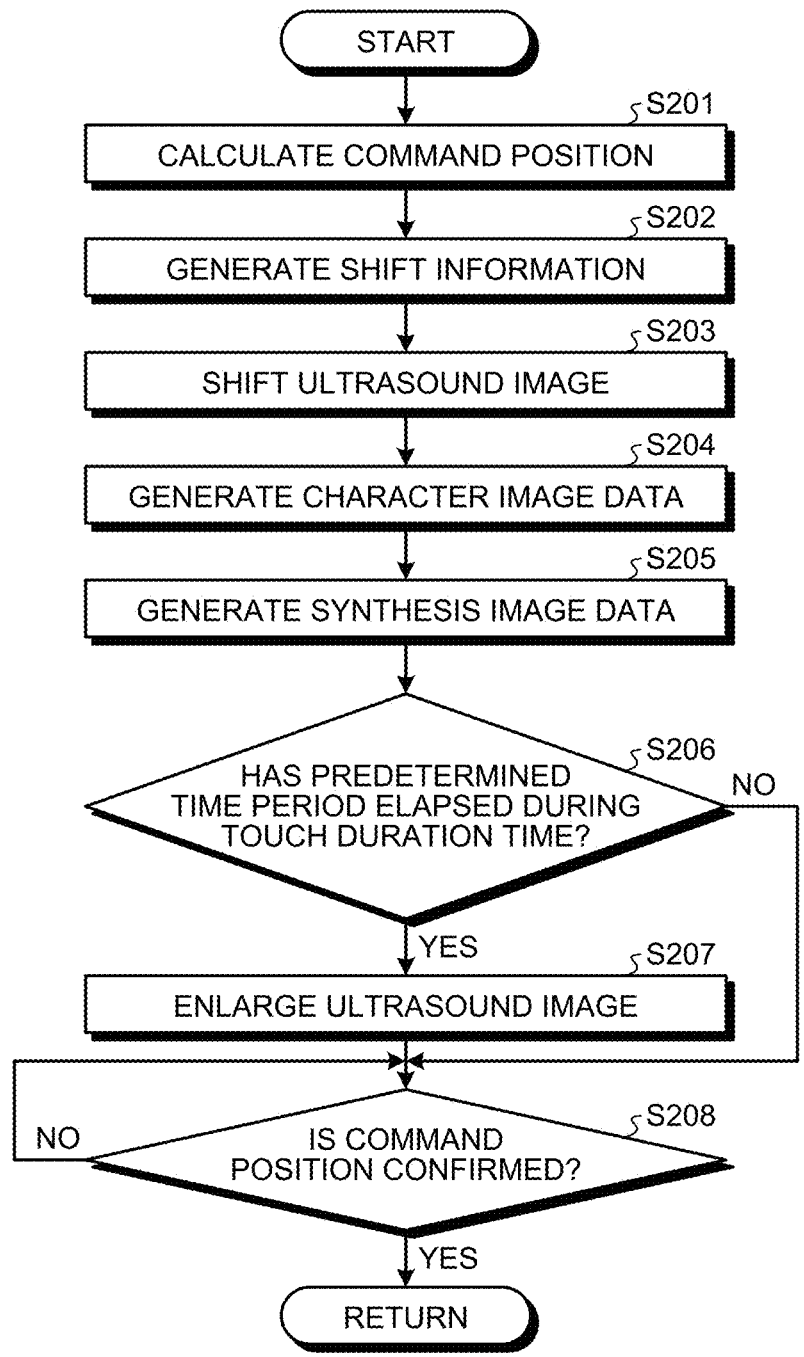
FIG. 3 is a flowchart that illustrates a measurement-point confirmation process performed by the ultrasound diagnosis system according to the first embodiment.

FIG. 3 is a flowchart that illustrates the measurement-point confirmation process performed by the ultrasound diagnosis system according to the first embodiment, and it is a flowchart that illustrates the first measurement-point confirmation process at Step S105. FIGS. 4 to 9 are diagrams that illustrate the measurement-point confirmation process according to the first embodiment.

Figure 4:
FIG. 4 is a diagram that illustrates the measurement-point confirmation process according to the first embodiment.
Figure 5:
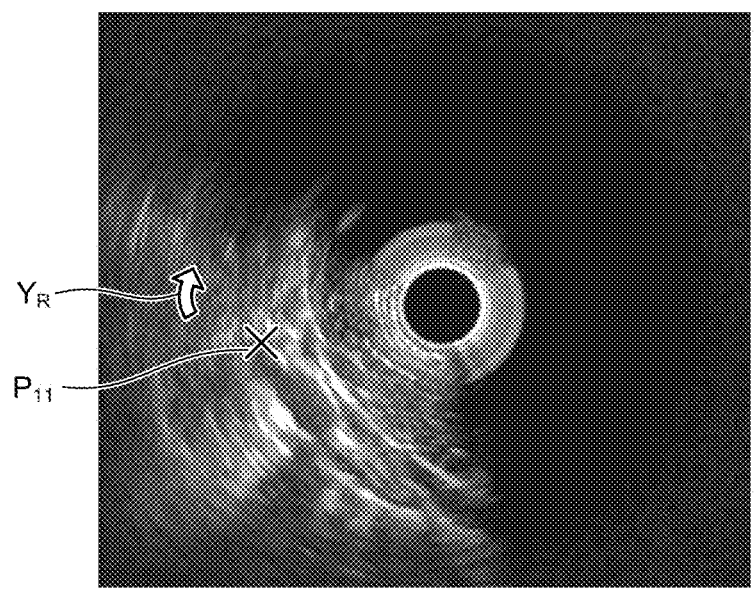
FIG. 5 is a diagram that illustrates the measurement-point confirmation process according to the first embodiment.
Figure 6:
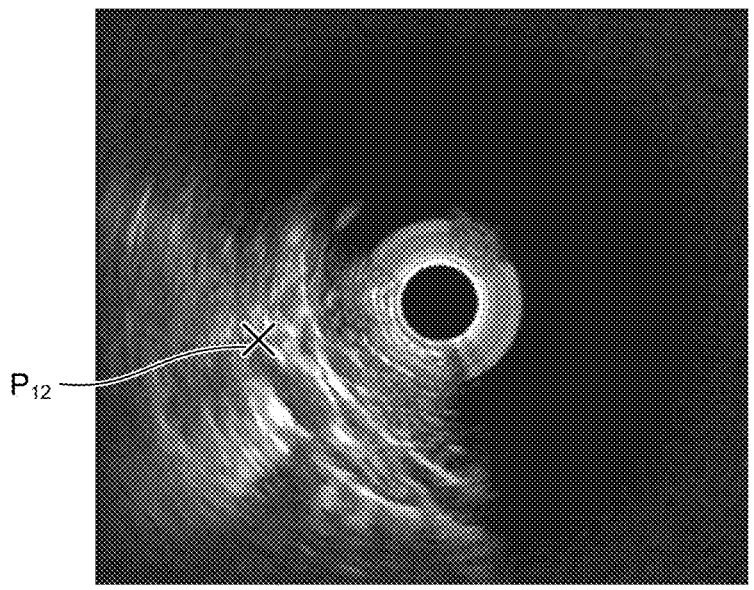
FIG. 6 is a diagram that illustrates the measurement-point confirmation process according to the first embodiment.
Figure 7:
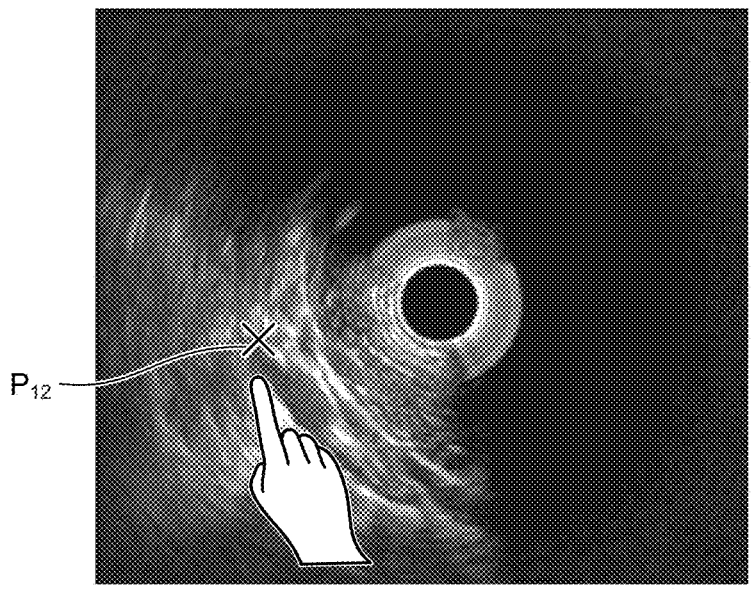
FIG. 7 is a diagram that illustrates the measurement-point confirmation process according to the first embodiment.

First, the command-position coordinates calculating unit 331 calculates the coordinates of the contact position (command position) of an object (finger) that is input to the touch panel 42 in accordance with the operating signal (Step S201, FIGS. 4, 5). As the coordinates of the command position, the command-position coordinates calculating unit 331 calculates the coordinates of the position with the highest pressure (signal value) within the contact position or the position at the center (center of gravity) of the area touched by the finger (the area to which a load is applied). For example, when an operating signal is input on a regular basis, the command-position coordinates calculating unit 331 calculates the command position (coordinates) each time an input is received.

Here, the character-image generating unit 34 may generate character image data including a character image (according to the first embodiment, a character image $P_{11}$ represented by "X", see FIG. 5) in accordance with the coordinates calculated by the command-position coordinates calculating unit 331. For example, with regard to the character image $P_{11}$, character image data is generated to allocate the character image $P_{11}$ in relation to the coordinates on the B-mode image such that the coordinates of the command position are located at the center (intersection point) of the mark "X". In this case, the image synthesizing unit 35 may generate synthesis image data including a synthesis image for display by synthesizing a B-mode image with a character image in a superimposed manner.

Then, the shift-information calculating unit 332 calculates the amount of shift of the B-mode image and outputs it as shift information (Step S202: a calculation step). If the ultrasound transducer in use is a radial-type ultrasound transducer, the shift-information calculating unit 332 generates shift information for rotating a B-mode image with the center of an image of the ultrasound transducer as a rotation center. In this case, the shift information includes a rotation direction and a rotation angle. For shifting a B-mode image, a direction (depth direction) along the depth from the ultrasound transducer 21 and the amount of shift in the depth direction as well as rotation may be set, or the control unit 38 may set any of the rotation and the depth direction in accordance with an input from a user or a command position.

After the shift-information calculating unit 332 generates the shift information, the ultrasound-image generating unit 32 shifts the B-mode image (ultrasound image) in accordance with the shift information (Step S203: a control step). According to the first embodiment, the ultrasound-image generating unit 32 rotates the B-mode image in a predetermined direction by a predetermined amount on the basis of the shift information.

For example, as illustrated in FIG. 5, the ultrasound-image generating unit 32 rotates the B-mode image by a predetermined amount in a rotation direction $Y_R$. The control unit 38 controls the character-image generating unit 34 so as to generate character image data where a character image is located at the position that corresponds to the command position on the B-mode image after the rotation process (Step S204: a character-image generation step). Then, the image synthesizing unit 35 synthesizes the B-mode image with the character image in a superimposed manner, thereby generating synthesis image data including a synthesis image for display (Step S205: a synthesis-image generation step). Due to this rotation process, the character image $P_{11}$ (see FIG. 5) indicating the command position is moved to a character image $P_{12}$ (see FIG. 6). Thus, on the B-mode image, the character image $P_{12}$ may be located at the command position input by the operator, and the character image $P_{12}$ may be displayed without being concealed with the operator's finger (see FIG. 7).

Then, the control unit 38 determines whether more than a predetermined time period has elapsed while the finger is continuously in contact with the same position on the touch panel 42 (Step S206). Here, when it is determined that the time period during which the finger is continuously in contact with the touch panel 42 is shorter than the predetermined time period (Step S206: No), the control unit 38 proceeds to Step S208. Conversely, when it is determined that more than the predetermined time period has elapsed while the finger is continuously in contact with the touch panel 42 (Step S206: Yes), the control unit 38 proceeds to Step S207. Furthermore, in the above explanation, the time period during which the finger is continuously in contact with the same position on the touch panel 42 is measured; however, this is not a limitation, and for example a duration time may be measured based on the assumption that the finger is continuously in contact with the touch panel 42 if the finger is continuously in contact within a specified range from the first contact position.

At Step S207, a process is performed to enlarge a partial area of the B-mode image including the command position. Here, to change an operation mode from the distance measurement mode, the control unit 38 causes the mode setting unit 36 to change the setting to the enlargement/reduction mode and gives a command to the ultrasound-image generating unit 32 so as to enlarge the image. The ultrasound-image generating unit 32 enlarges the B-mode image by a predetermined enlargement percentage and inputs the ultrasound image after the enlargement process to the image synthesizing unit 35. The ultrasound-image generating unit 32 may enlarge the image with the center position of the B-mode image as a center or may enlarge it with the command position (i.e., the character image $P_{11}$) as a center.

Figure 8:
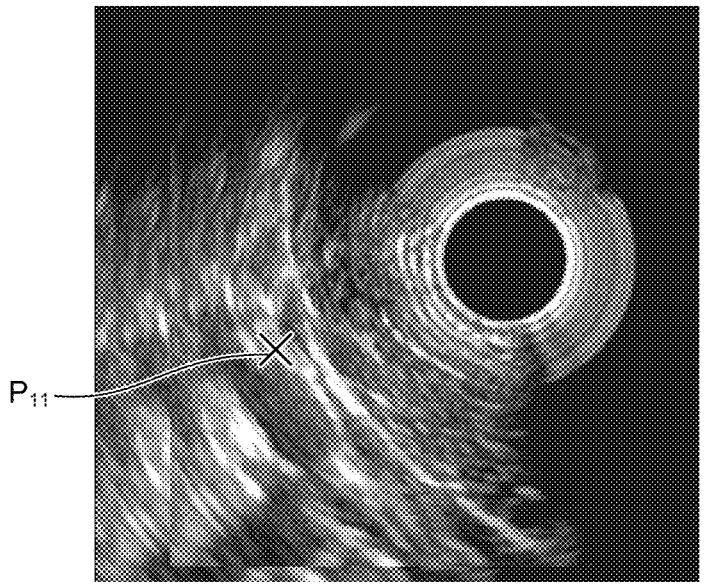
FIG. 8 is a diagram that illustrates the measurement-point confirmation process according to the first embodiment.
Figure 9:
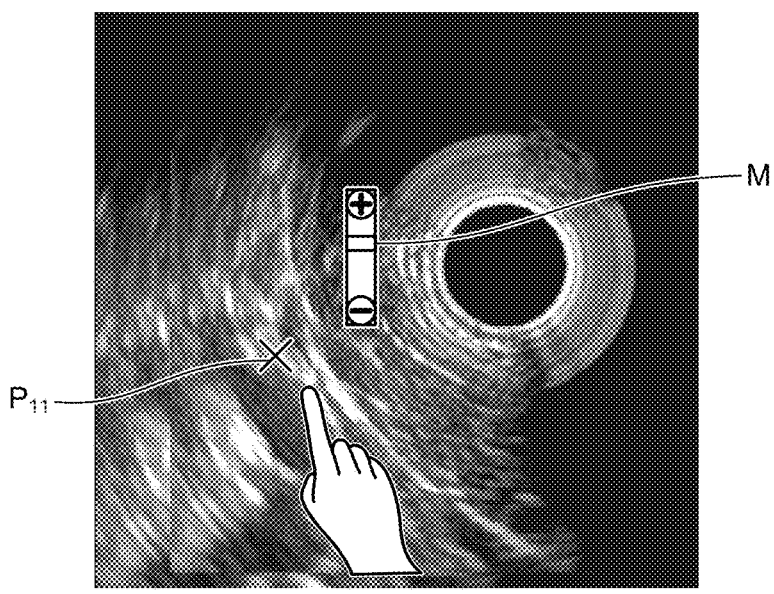
FIG. 9 is a diagram that illustrates the measurement-point confirmation process according to the first embodiment.

After the enlarged B-mode image generated by the ultrasound-image generating unit 32 is input, the image synthesizing unit 35 superimposes the character image $P_{11}$ on the enlarged B-mode image in accordance with the coordinates of the character image $P_{11}$ superimposed on the B-mode image before enlargement, thereby allocating the character image $P_{11}$ on the enlarged B-mode image (see FIG. 8). Then, the calculating unit 33, the character-image generating unit 34, and the image synthesizing unit 35 update a character image (command position) in accordance with an operating signal input from the touch panel 42. Thus, the position of the character image $P_{11}$ on the B-mode image may be finely adjusted.

Furthermore, in the enlargement/reduction mode, an enlargement percentage (display magnification) may be changed in accordance with changes in the contact position on the touch panel 42. For example, a threshold is set for the amount of change in a command position, and the control unit 38 performs control such that, when the amount of change in the command position exceeds the threshold, the command position is moved, and when the amount of change is lower than or equal to the threshold, the enlargement percentage of the B-mode image is changed. For example, when the enlargement/reduction mode is set, the control unit 38 displays an indicator M on the display unit 41. The control unit 38 increases (+) the enlargement percentage when a vector component of the direction (move vector) for changing a command position is identical to a vector (in a vertical direction in the case of FIG. 9) in the "+" direction or the "−" direction of the indicator M beyond a certain level, for example, when a vector quantity in an upward direction is large, a moving velocity in an upward direction is small, or a pressing force in an upward direction on a contact area is large, and decreases (−) the enlargement percentage when a vector quantity in a downward direction is large, a moving velocity in a downward direction is small, or a pressing force in a downward direction on a contact area is large. Furthermore, the minimum value of the enlargement percentage is larger than zero and it is the least enlargement percentage selected, and an image is enlarged to be larger than the originally displayed B-mode image. Furthermore, the indicator M may have the "+" direction and the "−" direction in a horizontal direction of an image. When the enlargement percentage is changed in a horizontal direction, the control unit 38 controls the enlargement percentage based on a vector in the same direction as the indicator M, the movement distance of a command position, and the like.

At Step S208 subsequent to Step S207, the control unit 38 determines whether an operation has been performed to set a measurement point by confirming a command position. When an operation has been performed to set a measurement point by confirming the command position (Step S208: Yes), the control unit 38 terminates the measurement-point confirmation process and returns to the flowchart in FIG. 2. Conversely, when an operation has not been performed to set a measurement point by confirming the command position (Step S208: No), the control unit 38 returns to Step S207 and repeatedly performs the above-described process. The operation to confirm a measurement point is performed, for example, when a command input for confirming a measurement point is received, when no operation is performed during a predetermined time period from the time when the finger is released from the touch panel 42, and the like.

Furthermore, after the position of one of the two measurement points is confirmed, the ultrasound-image generating unit 32 may move the B-mode image such that the position of the B-mode image that corresponds to the position where the character image $P_{11}$ (measurement point) is allocated is located at the center of the display screen of the display unit 41. Here, the character-image generating unit 34 generates character image data in which a character image has been moved in accordance with the moved B-mode image, i.e., the character image has been moved to the center.

Furthermore, in the explanation, the trigger for shifting to the enlargement mode is a duration time of touch at the same position; however, it may be the moving velocity of a finger (command position), a contact pressure to the touch panel 42, the combination thereof, tap, double tap, or the like. For example, if the moving velocity is a trigger, it is assumed that a command position is moved to a farther position as it is higher and a command position is moved to a closer position as it is lower, and a control is performed such that a transition is made to an enlargement mode when the moving velocity is low. Furthermore, when a transition is made to the enlargement mode due to single tap, double tap, or the like, the control unit 38 may perform control so as to make enlargement when double tap is conducted and make reduction when single tap is conducted. Users may previously register and edit operation performed to change the enlargement percentage.

With reference back to the flowchart in FIG. 2, after one measurement point is confirmed at Step S105, the control unit 38 determines whether an input (touch input) of a new operating signal has been received from the control unit 44 (the touch panel 42) (Step S106). When it is determined that an input (touch input) of a new operating signal has been received (Step S106: Yes), the control unit 38 proceeds to Step S107. Conversely, when no input of a new operating signal has been received (Step S106: No), the control unit 38 repeatedly checks whether an operating signal has been input.

After receiving an operating signal from the operating device 4, the control unit 38 performs a process to calculate and display a first command position based on the operating signal (Step S107: a second measurement-point confirmation process). Specifically, the calculating unit 33 performs a process to calculate the other one of the two measurement points (command positions) for measurement in accordance with a command input from the touch panel 42, and the operating device 4 causes the display unit 41 to display the measurement point (command position) superimposed on the B-mode image. The process to calculate and display the measurement point (command position) is the same as the flowchart illustrated in FIG. 3.

Figure 10:
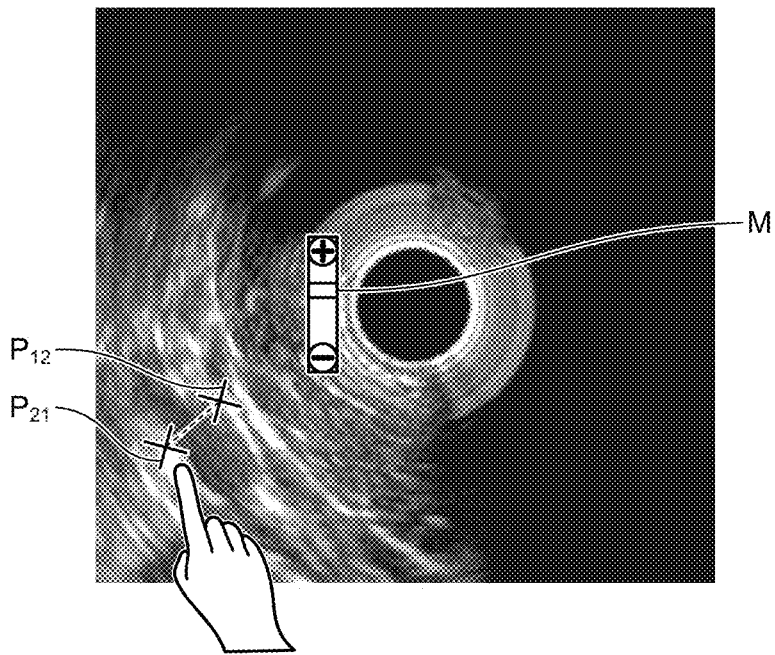
FIG. 10 is a diagram that illustrates the measurement-point confirmation process according to the first embodiment.

FIG. 10 is a diagram that illustrates the measurement-point confirmation process according to the first embodiment, and it is a diagram that illustrates the second measurement-point confirmation process at Step S107. At Step S107, when a command is input to the touch panel 42 due to the contact of the operator's finger, the display screen illustrated in FIG. 10 displays the B-mode image and a character image $P_{21}$, for which a position has been calculated in accordance with the command input and a rotation process has been performed on the B-mode image, in addition to the measurement point (the character image $P_{12}$) confirmed at Step S105 on the B-mode image.

Figure 11:
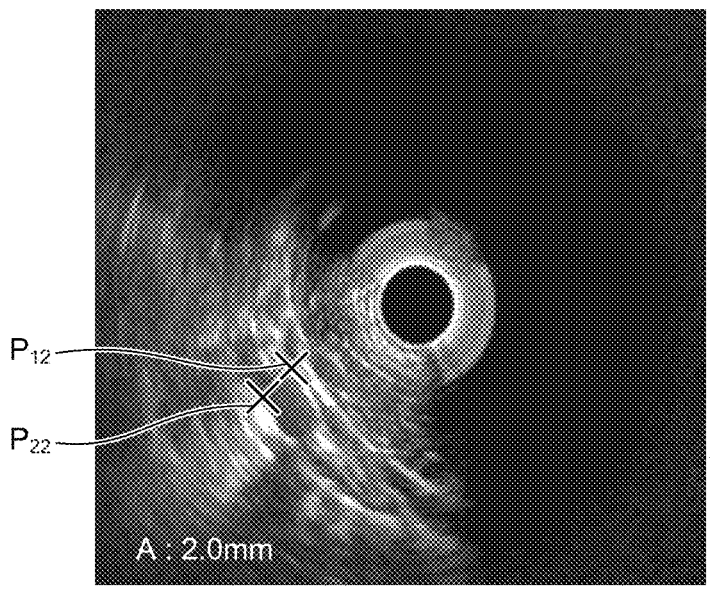
FIG. 11 is a diagram that illustrates the measurement-point confirmation process according to the first embodiment.

FIG. 11 is a diagram that illustrates the measurement-point confirmation process according to the first embodiment, and it is a diagram that illustrates the measurement points confirmed at Step S105 and S107. After the measurement point is confirmed at Step S107, the display screen illustrated in FIG. 11 displays the character image $P_{12}$ confirmed at Step S105 and a character image $P_{22}$ confirmed at Step S107 in a superimposed manner on the B-mode image.

After the positions (coordinates) of the two measurement points (the character images $P_{12}$, $P_{22}$) are calculated, the measurement-points distance calculating unit 333 calculates the distance between the character images $P_{12}$ and $P_{22}$ and displays it on the display unit 41 (Step S108). The measurement-points distance calculating unit 333 calculates the length of the line segment connecting the character images $P_{12}$, $P_{22}$ and calculates the actual value (A: 2.0 mm illustrated in FIG. 11) based on the calculated length. Then, the control unit 38 controls the display unit 41 so as to display the calculated actual value. Furthermore, the display device 5 may display the calculated distance between the measurement points and the actual value.

At Step S109 subsequent to Step S108, the control unit 38 determines whether a measurement termination command for the measurement-point confirmation process has been input. The control unit 38 determines whether the operating device 4 has received input of the measurement termination command and, when the operating device 4 has received input of the measurement termination command (Step S109: Yes), terminates the measurement process. Conversely, if the input unit 37 or the operating device 4 has not received input of the measurement termination command (Step S109: No), Step S103 is returned, and the above-described process is repeated. The measurement termination command includes, for example, a case where a command for terminating the distance measurement mode has been input, a case where no operation has been received during a predetermined time period, and the like.

Furthermore, with the above-described flow, an explanation is given of a case where the display unit 41 in the operating device 4 displays synthesis images; however, the display device 5 may display similar images, or the display device 5 may display only B-mode images during the measurement process. Furthermore, images displayed by the display unit 41 and the display device 5 may be identical or different images. The display device 5 may display not ultrasound images but measurement points only to make it possible to select whether an image is to be rotated, moved, or displayed in an enlarged manner.

According to the first embodiment described above, after a command position (coordinates) on a B-mode image is calculated in accordance with the contact position of the finger on the touch panel 42, the B-mode image is rotated, and the character image $P_{12}$ is allocated at the position that corresponds to the command position in the B-mode image, whereby with regard to the position (the character image $P_{11}$) specified by an operator, or the like, the character image $P_{12}$ is allocated in accordance with the position intuitively specified by the operator, and the visibility of the character image $P_{12}$ is retained without being hidden by the finger of the operator so that the operability regarding a command input of a command point on an ultrasound image (B-mode image) may be improved.

Furthermore, in the explanation according to the above-described first embodiment, two command positions are input at different timing in chronological order when a touch is made with one finger and then a touch is made with another finger; however, two command positions may be input by simultaneously touching the touch panel 42 with two fingers. When two command positions are simultaneously input, each measurement point is confirmed on the basis of each command position (contact position).

Furthermore, in the explanation according to the above-described first embodiment, a B-mode image is enlarged in the enlargement mode; however, the range for generating a B-mode image may be changed. When a B-mode image is enlarged, a partial area of the ultrasound image (B-mode image) generated by the ultrasound-image generating unit 32 is clipped and enlarged. However, when a B-mode image is enlarged by changing the range, ultrasonic waves are transmitted in accordance with the changed range, ultrasound echoes reflected by an observation target are acquired, and a B-mode image with the changed range is generated by the ultrasound-image generating unit 32. The subsequent process is the same as the above-described process. As described above, when the range is changed, the amount of change is set based on a touch duration time, the number of times touch is detected, and a preset amount of change.

Modification 1 of the First Embodiment

Figure 12:
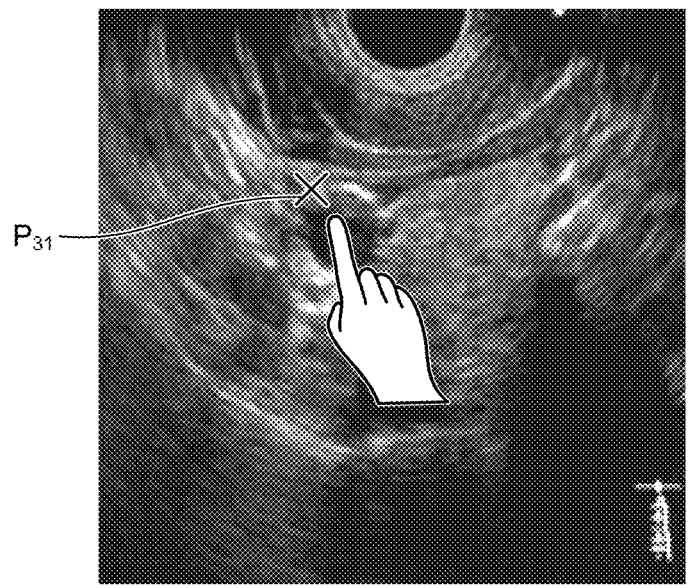
FIG. 12 is a diagram that illustrates a measurement-point confirmation process according to a modification 1 of the first embodiment.

FIG. 12 is a diagram that illustrates a measurement-point confirmation process according to a modification 1 of the first embodiment. According to the above-described first embodiment, a radial-type ultrasound transducer is explained as an example; however, this is not a limitation, and a convex-type and a linear-type ultrasound transducers are applicable. For example, as illustrated in FIG. 12, in the case of a convex-type ultrasound transducer, when a command position is input, a B-mode image is shifted in at least one direction of the display screen, i.e., an upward direction, a downward direction, a leftward direction, or a rightward direction, so that a control is performed such that a character image $P_{31}$ indicating the command position is not hidden by a finger of the operator. FIG. 12 illustrates an example where a B-mode image is shifted to a position in combination of the upward direction and the leftward direction and the character image $P_{31}$ is superimposed on the shifted B-mode image.

Furthermore, the control unit 38 is capable of identifying the type of the ultrasound transducer 21 provided in the ultrasound probe 2 connected to the processing device 3, and the shift-information calculating unit 332 generates shift information in accordance with the identified ultrasound transducer. The storage unit 39 stores the information for identifying the ultrasound transducer, and the control unit 38 acquires unique information from the connected ultrasound probe 2 and identifies the type of the ultrasound transducer provided in the connected ultrasound probe 2 on the basis of the acquired unique information and the information stored in the storage unit 39.

Modification 2 of the First Embodiment

Figure 13:
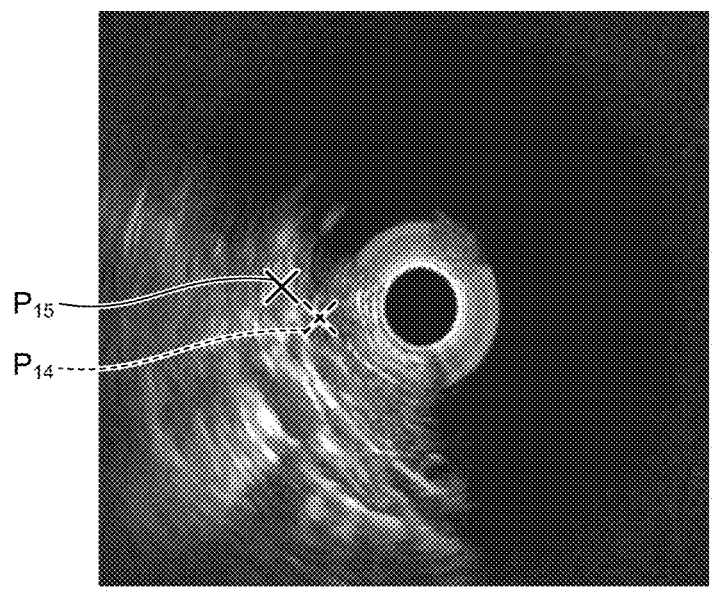
FIG. 13 is a diagram that illustrates a measurement-point confirmation process according to a modification 2 of the first embodiment.
Figure 14:
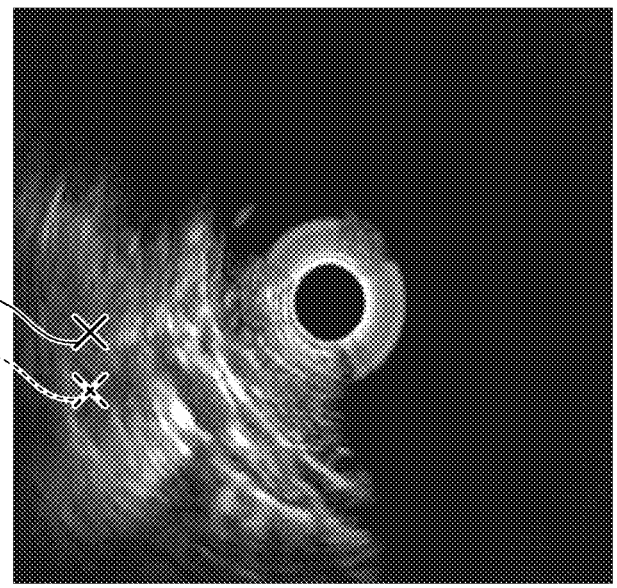
FIG. 14 is a diagram that illustrates the measurement-point confirmation process according to the modification 2 of the first embodiment.

Furthermore, a radial-type ultrasound transducer may shift synthesis images in upward, downward, rightward, and leftward directions of the screen as in the above-described modification 1. FIGS. 13 and 14 are diagrams that illustrate the measurement-point confirmation process according to a modification 2 of the first embodiment, and they are diagrams that illustrate shifted synthesis images. According to the modification 2, a slide direction of the synthesis image is changed in accordance with the depth of a command position from the ultrasound transducer.

For example, when the position of the character image (command position) is a position with a small depth from the ultrasound transducer like a character image $P_{14}$ illustrated in FIG. 13, the B-mode image is slid in an upper left direction of the display screen and a character image $P_{15}$ is displayed. Conversely, when the position of the character image (command position) is a position with a large depth from the ultrasound transducer like a character image $P_{16}$ illustrated in FIG. 14, the B-mode image is slid in an upward direction of the display screen and a character image $P_{17}$ is displayed. In this manner, shifting due to sliding as well as shifting due to rotation may be conducted, and a shift direction may be changed in accordance with a depth.

Modification 3 of the First Embodiment

Figure 15:
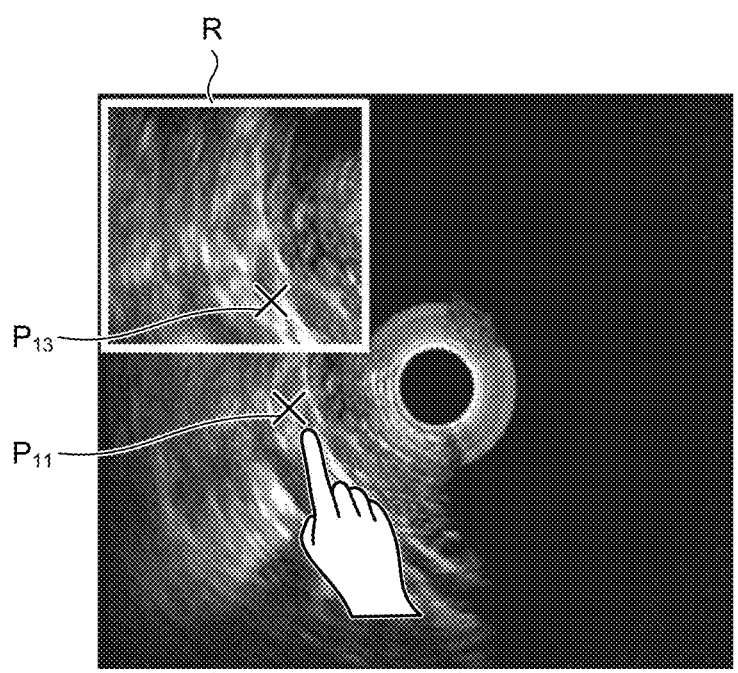
FIG. 15 is a diagram that illustrates a measurement-point confirmation process according to a modification 3 of the first embodiment.

FIG. 15 is a diagram that illustrates a measurement-point confirmation process according to a modification 3 of the first embodiment. According to the above-described first embodiment, an explanation is given of, for example, the configuration for enlarging a B-mode image while the display position of the character image $P_{11}$ is kept; however, this is not a limitation, and an enlarged image may be displayed on a different display area. For example, as illustrated in FIG. 15, a display area R for displaying an enlarged image is provided to display a synthesis image where a character image $P_{13}$ is allocated on the enlarged B-mode image. Furthermore, the character image $P_{13}$ on the B-mode image at the display area R is located at the position that corresponds to the character image $P_{11}$, and when the character image $P_{11}$ is moved, the position of the character image $P_{13}$ is accordingly changed. Furthermore, when the character image $P_{13}$ is out of the display area R due to movement of the character image $P_{11}$, the enlarged area of the B-mode image is changed to a partial area so that the character image $P_{13}$ is displayed on the display area R.

Second Embodiment

Figure 16:
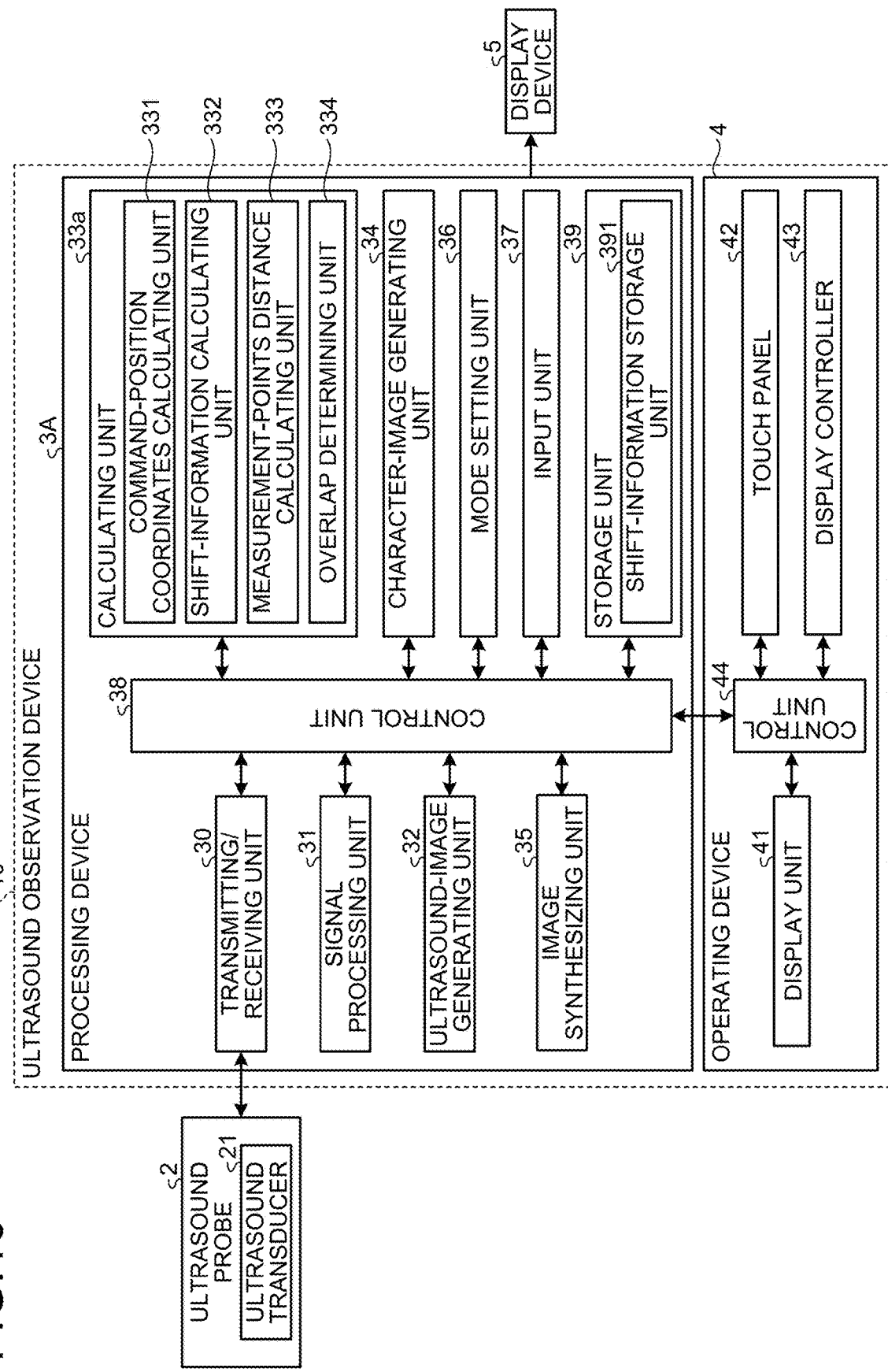
FIG. 16 is a block diagram that illustrates the configuration of an ultrasound diagnosis system according to a second embodiment.
Figure 17:
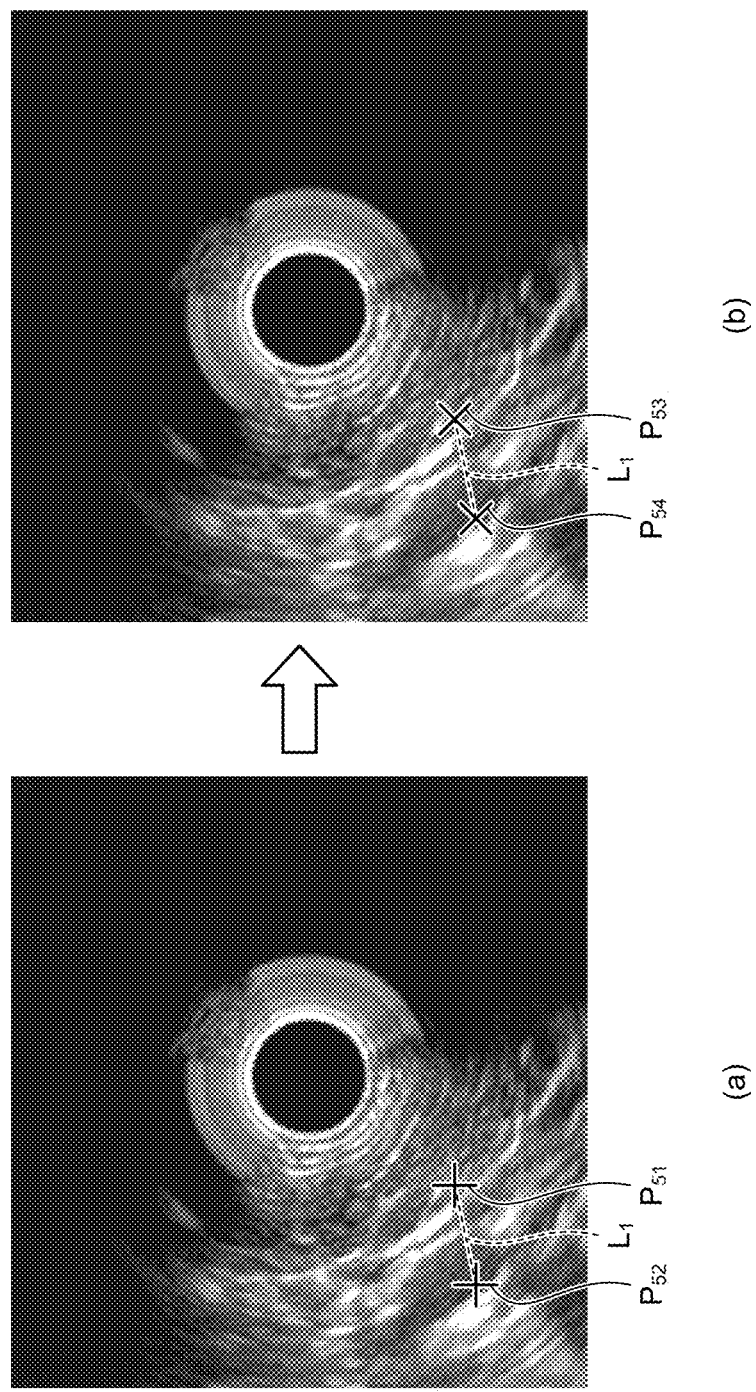
FIG. 17 is a diagram that illustrates a character-image display process according to the second embodiment.

Next, with reference to a drawing, an explanation is given of a second embodiment. FIG. 16 is a block diagram that illustrates the configuration of an ultrasound diagnosis system according to the second embodiment. FIG. 17 is a diagram that illustrates a character-image display process according to the second embodiment. According to the second embodiment, to improve the visibility of character images, two character images are rotated in accordance with location of the character images.

In an ultrasound diagnosis system 1A according to the second embodiment, as compared with the configuration of the above-described ultrasound diagnosis system 1, a calculating unit 33a in a processing device 3A further includes an overlap determining unit 334. The overlap determining unit 334 determines whether two character images are overlapped with the line segment connecting the two character images.

When two character images (character images $P_{51}$, $P_{52}$) are displayed in accordance with two measurement points that are set for distance measurement, a line segment $L_1$ connecting the character images $P_{51}$, $P_{52}$ is sometimes overlapped with the character images $P_{51}$, $P_{52}$, as illustrated in a part (a) of FIG. 17. In this case, the visibility of the center positions of the character images $P_{51}$, $P_{52}$ and the edges of the line segment $L_1$ are reduced.

According to the second embodiment, the overlap determining unit 334 determines whether a character image and a line segment are overlapped on the basis of the shape of the character image and the direction to which the line segment extends. The overlap determining unit 334 determines that the line segment $L_1$ connecting the character images $P_{51}$, $P_{52}$ are overlapped with the character images $P_{51}$, $P_{52}$, the shift-information calculating unit 332 generates shift information indicating that the character images are to be rotated, and the character-image generating unit 34 rotates the character images $P_{51}$, $P_{52}$ and generates character images $P_{53}$, $P_{54}$ that are not overlapped with the line segment $L_1$, as illustrated in a part (b) of FIG. 17. For example, the character-image generating unit 34 rotates a character image by 45° with the center of the character image as a rotation center, thereby generating character image data. Furthermore, in accordance with the positional relationship between the character images $P_{51}$, $P_{52}$, rotation may be made such that the line segment $L_1$ always passes through the center of the two perpendicular straight lines of the character images $P_{51}$, $P_{52}$.

According to the second embodiment described above, the advantage of the above-described first embodiment may be obtained, and when the overlap determining unit 334 determines that the line segment $L_1$ connecting the character images $P_{51}$, $P_{52}$ is overlapped with the character images $P_{51}$, $P_{52}$, the character-image generating unit 34 rotates the character images $P_{51}$, $P_{52}$ or rotates them such that, in accordance with the positional relationship between the character images $P_{51}$, $P_{52}$, the angle made between the line segments of the character images $P_{51}$, $P_{52}$ (two perpendicular straight lines) and the line segment $L_1$ is always 45° so that the generated character images $P_{53}$, $P_{54}$ are not overlapped with the line segment $L_1$, whereby it is possible to prevent a reduction in the visibility of the center of a character image and the edges of a measurement range.

Furthermore, in the explanation according to the above-described second embodiment, the character images $P_{51}$, $P_{52}$ are rotated to change the shapes of the character images; however, when the overlap determining unit 334 determines that they are overlapped, a character image may be changed from "X" to a triangle, a circle, or the like.

Third Embodiment

Figure 18:
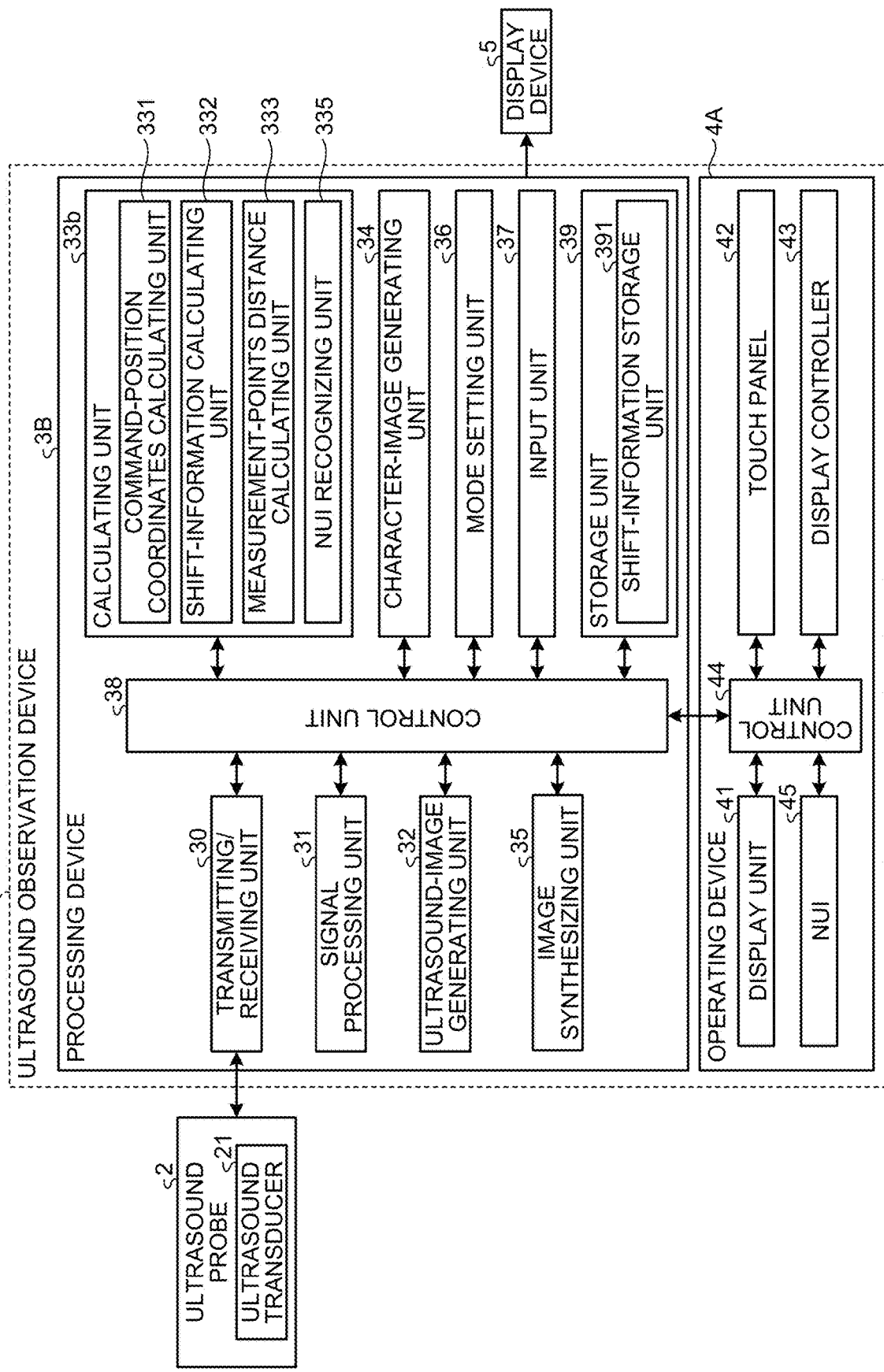
FIG. 18 is a block diagram that illustrates the configuration of an ultrasound diagnosis system according to a third embodiment.

Next, a third embodiment is explained with reference to drawings. FIG. 18 is a block diagram that illustrates the configuration of an ultrasound diagnosis system according to the third embodiment. According to the third embodiment, to improve the visibility of character images, the line of sight of an operator is detected, and a character image is shifted in accordance with a detection result.

In an ultrasound diagnosis system 1B according to the third embodiment, as compared with the configuration of the above-described ultrasound diagnosis system 1, a calculating unit 33b of a processing device 3B further includes an NUI recognizing unit 335, and an operating device 4A further includes a natural user interface (NUI) 45. The NUI 45 captures for example the upper half of the body of an operator and outputs identification information for identifying an eye (the line of sight) or a finger. On the basis of identification information from the NUI 45, the NUI recognizing unit 335 detects the direction of the line of sight of the operator or detects whether the hand touching the touch panel 42 is a right hand or a left hand and outputs it to the shift-information calculating unit 332. The NUI recognizing unit 335 compares the obtained electric signal with feature data to recognize the direction of the line of sight or a right hand or a left hand.

Figure 19:
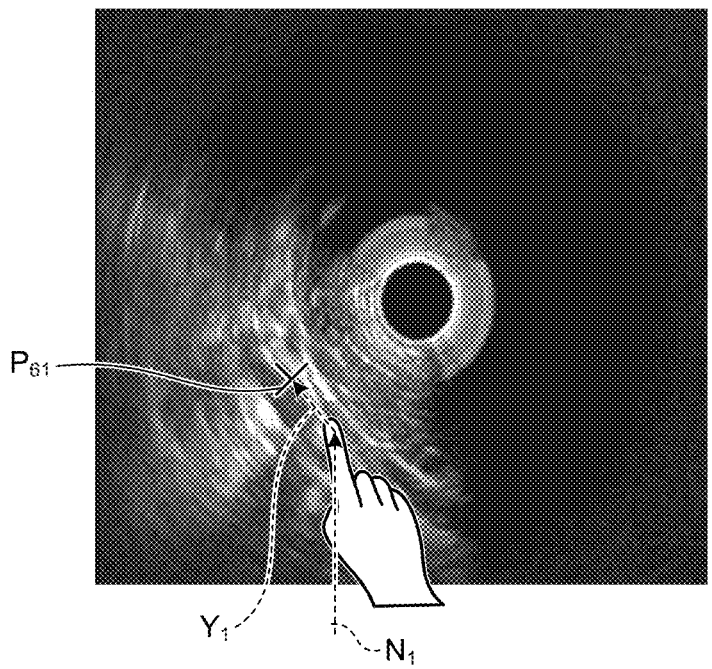
FIG. 19 is a diagram that illustrates a measurement-point confirmation process according to a third embodiment.
Figure 20:
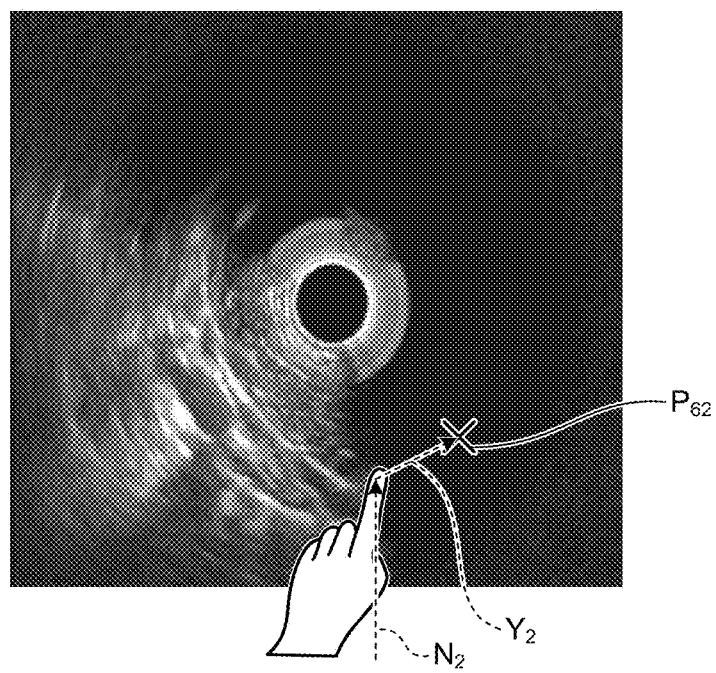
FIG. 20 is a diagram that illustrates the measurement-point confirmation process according to the third embodiment.

FIGS. 19, 20 are diagrams that illustrate a measurement-point confirmation process according to the third embodiment. For example, when the NUI recognizing unit 335 obtains a recognition result such that the hand touching the touch panel 42 is a right hand and the direction of the line of sight is an $N_1$ direction, the shift-information calculating unit 332 sets a shift direction such that the character image is moved to the left side that is the side of the thumb and the front of the line of sight. In FIG. 19, the shift direction is set in a direction (an arrow $Y_1$ in FIG. 19) along which the character image is moved to the upper left. Thus, as illustrated in FIG. 19, a character image $P_{61}$ is an image displayed on the upper left of the fingertip.

Furthermore, when the NUI recognizing unit 335 obtains a recognition result such that the hand touching the touch panel 42 is a left hand and the direction of the line of sight is an $N_2$ direction, the shift-information calculating unit 332 sets a shift direction such that the character image is moved to the right side that is the side of the thumb and the front of the line of sight. In FIG. 20, the shift direction is set in a direction (an arrow $Y_2$ in FIG. 20) along which the character image is moved to the upper right. Thus, as illustrated in FIG. 20, a character image $P_{62}$ is an image displayed on the upper right of the fingertip.

According to the third embodiment described above, the advantage of the above-described first embodiment may be obtained, and the NUI recognizing unit 335 detects the direction of the line of sight of an operator and detects whether the hand touching the touch panel 42 is a right hand or a left hand on the basis of identification information from the NUI 45, and the shift-information calculating unit 332 determines a shift direction in accordance with the direction of the line of sight and the hand so that a character image is allocated based on the position that is intuitively designated by the operator and the visibility of the character image is retained, whereby the operability with regard to a command input for a command point on an ultrasound image (B-mode image) may be further improved.

Furthermore, in the explanation according to the above-described third embodiment, the NUI 45 outputs identification information for identifying an eye (the line of sight) or a hand; however, at least one of the line of sight and a hand may be detected.

Furthermore, in the explanation according to the first to the third embodiments and the modifications described above, the observation target is for example a living tissue; however, industrial-use endoscopes for observing the characteristics of a material are also applicable. The ultrasound observation device according to the present disclosure is applicable regardless of whether it is inside or outside a body. Moreover, not only ultrasonic waves but also infrared rays, or the like, may be emitted to transmit and receive signals of the observation target.

Furthermore, in the explanation according to the first to the third embodiments and the modifications described above, the distance between two measurement points is measured; however, when the measurement target is a circle, or the like, and an area is measured, a measurement point may be regarded as the diameter of the circle, and the diameter of the circle as the measurement target may be set by operation on the touch panel. Moreover, when an ellipse is set rather than a circle, any one of the short axis and the long axis calculated at a predetermined percentage may be input through the touch panel 42. For example, not only measuring the distance between two measurement points, but also an operation target position may be determined on the basis of input of one point or three or more points.

Thus, the present disclosure may include various embodiments without departing from the technical idea disclosed in claims.

According to the present disclosure, there is an advantage such that operability with regard to a command input of a command point on an ultrasound image may be improved.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A processing device comprising a controller comprising hardware, wherein the controller being configured to:
   generate an ultrasound image based on an ultrasound signal acquired by an ultrasound probe, the ultrasound probe being configured to transmit an ultrasonic wave to a subject that is an observation target and receive an ultrasonic wave reflected by the subject;
   generate a rotation amount including a rotation direction and rotation angle of a display area of the ultrasound image displayed on a display unit in response to a command position with respect to the ultrasound image displayed on the display unit;
   rotate the ultrasound image by the rotation amount;
   generate a character image indicating a position corresponding to the command position in the rotated ultrasound image; and
   display the rotated ultrasound image on the display unit and superimpose the character image at the position corresponding to the command position on the rotated ultrasound image displayed on the display unit.

2. The processing device according to claim 1, wherein the controller is configured to generate the rotated ultrasound image by changing a display magnification or a range for generating an ultrasound image, in accordance with a behavior of a command position of the area targeted for a process performed on the ultrasound image during a duration time of a touch on a touch panel provided on a display surface of the display unit configured to display the ultrasound image and the rotated ultrasound image, the touch panel including a contact surface with which a finger of an operator is brought into contact, and receiving an input that corresponds to a contact position of the finger as the command position.

3. The processing device according to claim 2, wherein the controller is further configured to display, on the display unit, the rotated ultrasound image generated by enlarging a partial area of the ultrasound image including the command position when the display magnification of the ultrasound image or the range for generating the ultrasound image is changed.

4. The processing device according to claim 2, wherein the behavior of the command position during a duration time of touch on the touch panel is a duration time of touch on an identical command position, and
the controller is configured to generate the rotated ultrasound image by changing the display magnification on the display unit or the range for generating when the duration time of touch is a predetermined time period or more.

5. The processing device according to claim 1, wherein the controller is configured to generate the rotated ultrasound image by changing the display magnification on the display unit or the range for generating in accordance with a number of times touch on the touch panel is detected.

6. The processing device according to claim 1, wherein the controller is further configured to set a shift direction of the display area of the ultrasound image in accordance with a type of an ultrasound transducer that is provided in the ultrasound probe connected to the processing device.

7. The processing device according to claim 1, wherein the controller is further configured to:
identify a type of the ultrasound probe connected to the processing device; and
set a shift direction of the display area of the ultrasound image in any of a rotation direction and a depth direction of the ultrasound transducer when the ultrasound probe connected to the processing device includes a radial-type ultrasound transducer.

8. The processing device according to claim 1, wherein the controller is further configured to:
identify a type of the ultrasound probe connected to the processing device; and
set a shift direction of the display area of the ultrasound image in at least one of upward, downward, rightward, and leftward directions of a display screen of the display unit when the ultrasound probe connected to the processing device includes a convex-type ultrasound transducer.

9. The processing device according to claim 6, wherein the controller is further configured to set a shift direction of the display area of the ultrasound image in accordance with the command position and a depth that is a depth from the ultrasound transducer and that is a depth from an image of the ultrasound transducer in the ultrasound image to a position that corresponds to the command position.

10. The processing device according to claim 1, wherein the controller is further configured to:
measure a distance between two command positions designated in the ultrasound image through a touch panel; and
generate the rotated ultrasound image in which, after input of one of the two command positions is terminated, a position that corresponds to the one of the command positions is located at a center of a display screen of the display unit.

11. The processing device according to claim 10, wherein the controller is further configured to change the character image in accordance with a positional relationship between character images that correspond to the two command positions.

12. The processing device according to claim 1, wherein the controller is further configured to set a shift direction of the display area of the ultrasound image in accordance with a detection result of a detector configured to detect at least one of a finger and a line of sight of an operator who operates a touch panel.

13. The processing device according to claim 1, wherein a center of the character image is positioned at coordinates of the command position.

14. A method of operating a processing device, comprising:
generating an ultrasound image based on an ultrasound signal acquired by an ultrasound probe, the ultrasound probe being configured to transmit an ultrasonic wave to a subject that is an observation target and receive an ultrasonic wave reflected by the subject;
generating a rotation amount including a rotation direction and rotation angle of a display area of the ultrasound image displayed on a display unit in response to a command position with respect to the first ultrasound image displayed on the display unit;
rotate the ultrasound image by the rotation amount;
generating a character image indicating a position corresponding to the command position in the rotated ultrasound image; and
displaying the rotated ultrasound image on the display unit and superimposing the character image at the position corresponding to the command position on the rotated ultrasound image displayed on the display unit.

15. A non-transitory computer-readable recording medium on which an executable program is recorded, the program instructing a processor to execute:
generating an ultrasound image based on an ultrasound signal acquired by an ultrasound probe, the ultrasound probe being configured to transmit an ultrasonic wave to a subject that is an observation target and receive an ultrasonic wave reflected by the subject;
generating a rotation amount including a rotation direction and rotation direction of a display area of the ultrasound image displayed on a display unit in response to a command position with respect to the ultrasound image displayed on the display unit;
rotating the ultrasound image by the rotation amount;
generating a character image indicating a position corresponding to the command position in the rotated ultrasound image; and
displaying the rotated ultrasound image on the display unit and superimposing the character image at the position corresponding to the command position on the rotated ultrasound image displayed on the display unit.

* * * * *